(12) United States Patent
Shigemori

(10) Patent No.: US 7,843,329 B2
(45) Date of Patent: Nov. 30, 2010

(54) RECEIVED INFORMATION TRANSFERRING APPARATUS, RECEIVING APPARATUS AND RECEIVED INFORMATION TRANSFERRING SYSTEM

(75) Inventor: Toshiaki Shigemori, Hachioji (JP)

(73) Assignee: Olympus Medical Systems Corp. (JP)

( * ) Notice: Subject to any disclaimer, the term of this patent is extended or adjusted under 35 U.S.C. 154(b) by 776 days.

(21) Appl. No.: 11/576,988

(22) PCT Filed: Sep. 8, 2006

(86) PCT No.: PCT/JP2006/017867
§ 371 (c)(1),
(2), (4) Date: Apr. 10, 2007

(87) PCT Pub. No.: WO2007/029817
PCT Pub. Date: Mar. 15, 2007

(65) Prior Publication Data
US 2008/0304240 A1    Dec. 11, 2008

(30) Foreign Application Priority Data
Sep. 9, 2005    (JP) .............................. 2005-263114

(51) Int. Cl.
*G08B 1/08* (2006.01)
(52) U.S. Cl. .............................. 340/539.12; 340/10.42; 340/572.1; 340/572.4; 340/572.8; 340/286.05; 340/568.1; 340/686.1; 600/109; 600/160; 600/301; 600/407

(58) Field of Classification Search ............ 340/539.12, 340/10.42, 572.1, 572.4, 572.8, 286.05, 568.1, 340/686.1; 600/109, 160, 301, 407
See application file for complete search history.

(56) References Cited

U.S. PATENT DOCUMENTS

2003/0085994 A1    5/2003    Fujita et al.
2004/0145871 A1*   7/2004    Lee ............................ 361/732

FOREIGN PATENT DOCUMENTS

| JP | 2001-231186 | 8/2001 |
|----|-------------|--------|
| JP | 2003-135389 | 5/2003 |
| JP | 2003-195730 | 7/2003 |
| JP | 2004-213841 | 7/2004 |
| JP | 2004-227071 | 8/2004 |
| JP | 2002-198789 | 7/2005 |
| JP | 2005-245712 | 9/2005 |
| WO | WO 2005/067781 A1 | 7/2005 |

OTHER PUBLICATIONS

International Search Report in PCT/JP2006/317867 dated Mar. 15, 2007.
International Search Report PCT/JP2006/317867.

* cited by examiner

*Primary Examiner*—Tai T Nguyen
(74) *Attorney, Agent, or Firm*—Ostrolenk Faber LLP

(57) ABSTRACT

In order to maintain stability when connected, a cradle 27 includes an engagement part 33 for engaging with regard to a unit connection part which allows an antenna unit having at least a receiving antenna to be detachably connected to a receiving unit constituting a receiving apparatus together with the antenna unit; and a connecting terminal 31 provided so as to be communicably connected to a connector provided to the receiving unit only when the unit connection part and the engagement part are in engaged state.

5 Claims, 7 Drawing Sheets

RECEIVED INFORMATION TRANSFERRING APPARATUS, RECEIVING APPARATUS AND RECEIVED INFORMATION TRANSFERRING SYSTEM

CROSS REFERENCE TO RELATED APPLICATION

The present application is a 35 U.S.C. §§371 national phase conversion of PCT/JP2006/317867, filed 8 Sep. 2006, which claims priority of Japanese Patent Application No. 2005-263114 filed 9 Sep. 2005, which is herein, incorporated by reference. The PCT Application was published in the Japanese Language.

TECHNICAL FIELD

The present invention relates to a received information transferring apparatus, a receiving apparatus and a received information transferring system, and more particularly to a received information transferring apparatus capable of maintaining a received information transferring apparatus stably under connected state and a receiving apparatus connected to the received information transferring apparatus and a received information transferring system including the received information transferring apparatus and receiving apparatus.

BACKGROUND ART

In recent years, capsule endoscopes (swallowable endoscopes in pill shape for medical use) which can be introduced from the mouth into body cavity and are designed to acquire information in the living body cavity through imaging or the like inside of digestive organs such as stomach or the like have been developed. As capsule endoscope of this sort, those incorporating in a capsule an illuminating unit composed of LED or the like, a solid-state imaging element composed of CCD, CMOS or the like, a transmitter for transmitting to the outside image data obtained by the solid-state imaging element, and a power supply unit composed of a battery or the like for driving these illuminating unit, solid-state imaging element and transmitter have been proposed (for example, see Patent Document 1).

When performing clinical examination using a capsule endoscope, electric wave transmitted by a capsule swallowed by a subject is caught by receiving antennae pasted at more than one portion, for example, eight portions, on the surface of the subject body, data thus caught are sent to a receiving apparatus via antenna cable, and is recorded by the receiving apparatus into CF memory or the like. Although it takes, for example, 8 to 10 hours until the clinical examination is completed, the subject is able to continue normal life while equipped with the receiving antennae and receiving apparatus. Upon completion of measurements by the capsule endoscope, the subject submits the receiving apparatus or the like to the hospital, hospital side then plugs the receiving apparatus into a cradle, and all measurement data recorded in the receiving apparatus are taken in a workstation which is connected to the cradle via USB cable. Following this, measurement results are observed as moving images on the workstation.

Patent Document: Japanese Patent Application Laid-Open No. 2001-231186

DISCLOSURE OF INVENTION

Problem to be Solved by the Invention

However, there is such a problem that if a receiving apparatus is plugged into a cradle while receiving antennae are connected, the cradle becomes unstable and the receiving apparatus is disengaged from the cradle while recorded measurement data are taken from the receiving apparatus to the workstation.

The present invention has been developed in view of the foregoing, and an object of the present invention is to provide a received information transferring apparatus, a receiving apparatus and a received information transferring system which are stable under connected state.

Means for Solving Problem

A received information transferring apparatus according to one aspect of the present invention includes an engagement part for engaging with regard to a unit connection part which allows an antenna unit having at least a receiving antenna to be detachably connected to a receiving unit constituting a receiving apparatus together with the antenna unit; and a communication connector that is provided so as to be communicably connected to a connector provided to the receiving unit only when the unit connection part and the engagement part are in an engaged state.

In the received information transferring apparatus the engagement part may be formed so as to be protruding to a portion where the antenna unit is mounted to the receiving unit, when the receiving unit is mounted to the received information transferring apparatus.

In the received information transferring apparatus, the engagement part is may be formed such that a length from a lower end of the receiving unit to an upper end of the engagement part, in a state where the receiving unit is mounted to the received information transferring apparatus, becomes longer than a length from the lower end of the receiving unit to a lower end of a convex part provided to the antenna unit, in a state where the antenna unit is mounted to the receiving unit, and when it is attempted to electrically connect the receiving apparatus, in the state where the antenna unit is mounted to the receiving unit, the upper end of the engagement part and the lower end of the convex part may interfere with each other.

A receiving apparatus according to another aspect of the present invention includes an antenna unit to which a receiving antenna is connected and that executes a receiving processing of a radio signal received by the receiving antenna; and a receiving unit to which the antenna unit is detachably mounted and that executes various processings based on a received signal received by the antenna unit. In the receiving apparatus, the receiving unit can be electrically connected to a received information transferring apparatus via a connector of the receiving unit and a communication connector of the received information transferring apparatus, a convex part is provided to the antenna unit, the convex part is formed such that a length from a lower end of the receiving unit to a lower end of the convex part, in a state where the antenna unit is mounted to the receiving unit, is shorter than a length from the lower end of the receiving unit to an upper end of an engagement part provided on the received information transferring apparatus, in a state where the receiving unit is mounted to the received information transferring apparatus, and when it is attempted to electrically connect to the received information transferring apparatus, in the state where the antenna unit is mounted to the receiving unit, the upper end of the engagement part and the lower end of the convex part interfere with each other.

A received information transferring system according to still another aspect of the present invention includes a receiving apparatus having an antenna unit to which a receiving antenna is connected and which executes a receiving processing of a radio signal received by the receiving antenna and a receiving unit to which the antenna unit is detachably connected and which executes various processings based on a received signal received by the antenna unit; and a received information transferring apparatus that can be electrically connected to the receiving unit via a connector of the receiving unit and a communication connector of the received information transferring apparatus. In the received information transferring system, a convex part is provided to the antenna unit and an engagement part is provided to the receiving unit, the convex part and the engagement part are formed such that a length from a lower end of the receiving unit to an upper end of the engagement part, in a state where the receiving unit is mounted to the received information transferring apparatus, is longer than a length from the lower end of the receiving unit to a lower end of the convex part, in a state where the antenna unit is mounted to the receiving unit, and when it is attempted to electrically connect the receiving apparatus to the received information transferring apparatus, in the state where the antenna unit is mounted to the receiving unit, the upper end of the engagement part and the lower end of the convex part interfere with each other.

EFFECT OF THE INVENTION

In the received information transferring apparatus, receiving apparatus and received information transferring system according to the present invention, since a communication connector can be communicably connected to a connector provided to the receiving unit only when an engagement part for engaging with regard to a unit connection part which allows an antenna unit having at least a receiving antenna to be detachably connected to a receiving unit constituting a receiving apparatus together with the antenna unit is in engaged state with the unit connection part, it is possible to stabilize the received information transferring apparatus in connected state.

EXPLANATIONS OF LETTERS OR NUMERALS

Figure 1:
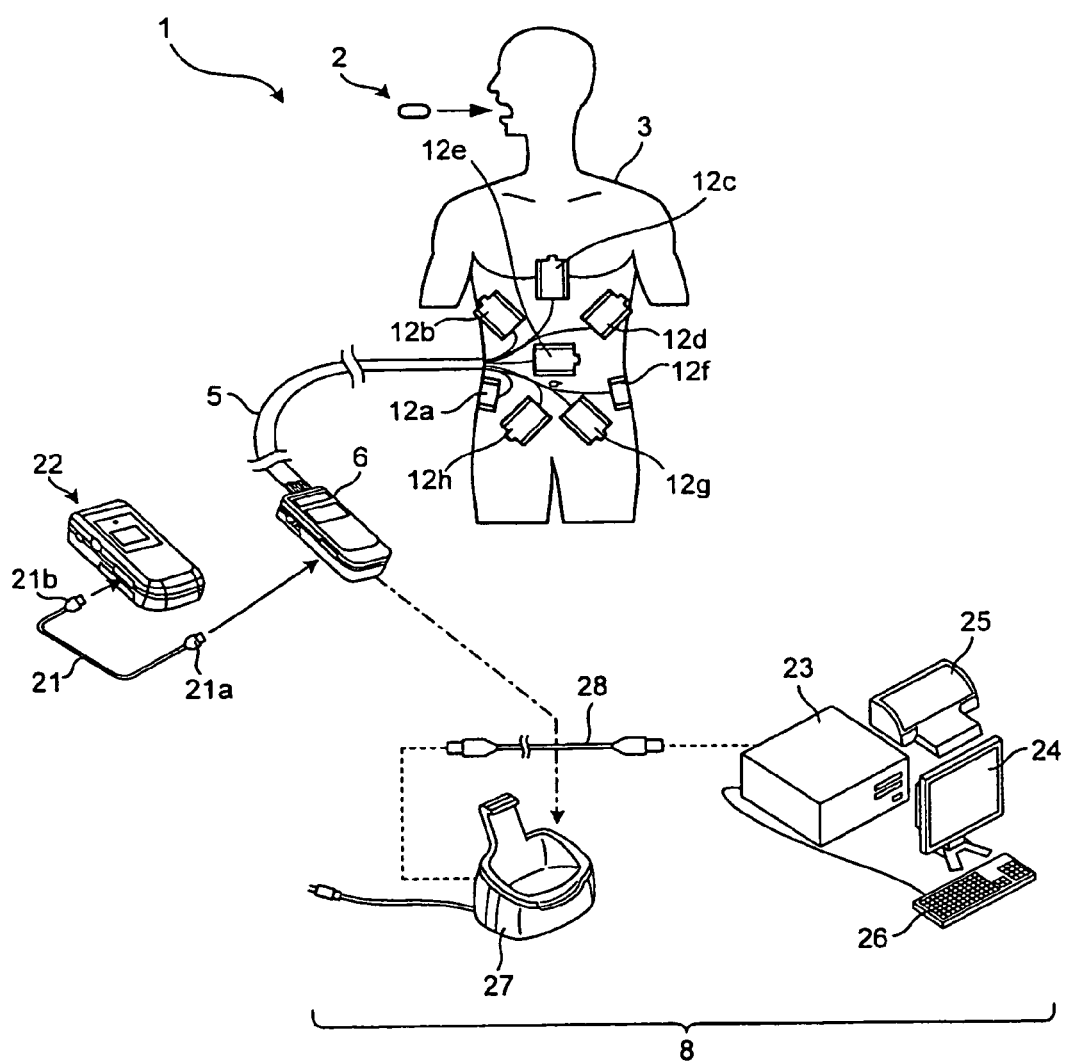
FIG. 1 is a diagram showing an example of a whole composition of a capsule endoscope system including a cradle according to a first embodiment.

1 Capsule endoscope system
2 Capsule endoscope
3 Subject
5 Cable
6, 46 Receiving apparatus
6a, 46a Receiving unit
6b, 46b Antenna unit
8 Workstation
12a, 12b, 12c, 12d, 12e, 12f, 12g, 12h Receiving antennae
16 Liquid crystal display unit
17 Antenna unit mounting part
18 Viewer cable connector
19 Connector
20 Eject button
21 Viewer cable
22 Viewer
23 Workstation main body
24 Display device
25 Printer
26 Keyboard
27, 37, 57 Cradle
28 Cradle cable
30, 60 Concave part
31, 61 Connecting terminal
32 Backrest
33, 43, 63 Protruding portion
50 Convex part

BEST MODE FOR CARRYING OUT THE INVENTION

Referring now to the drawings, embodiments of the received information transferring apparatus (cradle), receiving apparatus, and received information transferring system (cradle system) of the present invention will be explained hereafter. In the embodiments shown below, an example where the cradle, receiving apparatus, and cradle system of the present invention are applied to the capsule endoscope system is shown. However, the present invention is in no way restricted by such specific embodiments.

First Embodiment

Figure 2:
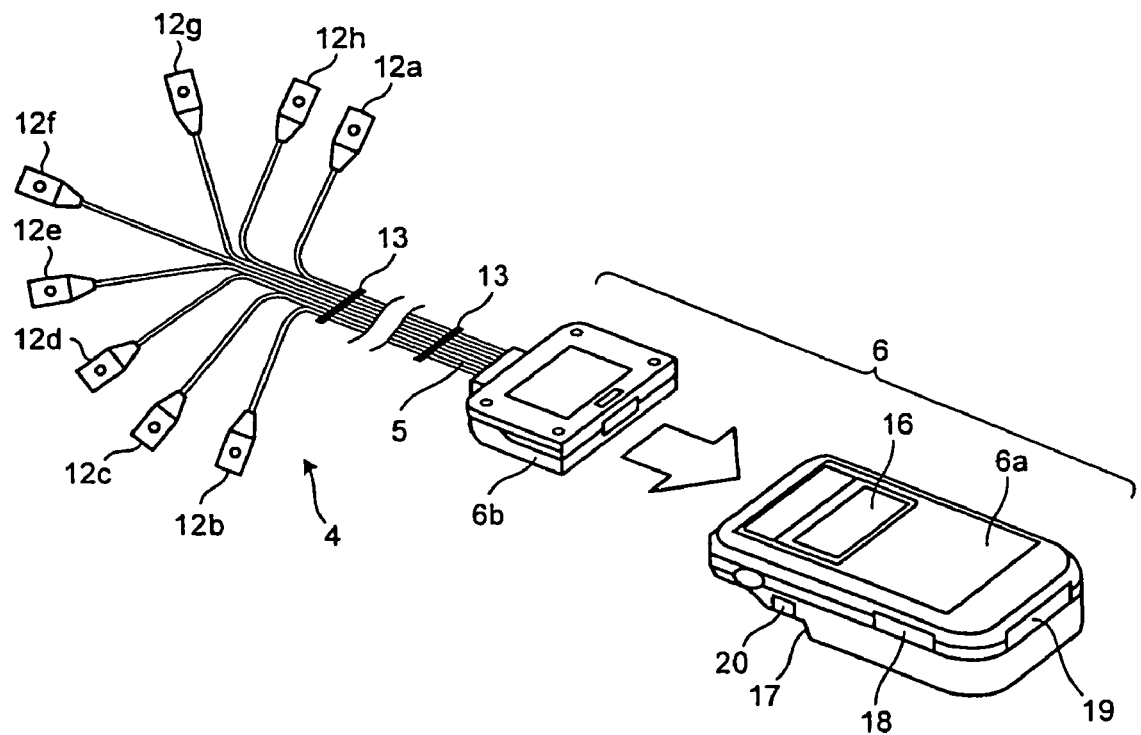
FIG. 2 is a perspective view showing a receiving antenna and receiving apparatus according to the first embodiment.

FIG. 1 is a drawing showing an example of a whole composition of the capsule endoscope system including the cradle according to a first embodiment, and FIG. 2 is a perspective view showing the receiving antenna and receiving apparatus. A capsule endoscope system 1 primarily includes a capsule endoscope 2; receiving antennae 12a to 12h having loop antenna structure directly mounted by adhesion or the like to predetermined sites on the surface of a subject 3; a receiving apparatus 6 as a portable clinical equipment which is electrically connected to these receiving antennae 12a to 12h by a cable 5 and records results of detection; and a workstation 8 provided at other than the subject 3.

It is possible for the subject 3 to swallow the capsule endoscope 2 which incorporates an imaging device; an illuminating device; a signal processor; a transmitter; and a power supply or the like (not shown). This capsule endoscope 2 swallowed by the subject 3 is introduced in the body cavity, takes images of imaging sites illuminated by the illuminating device such as LED or the like by the imaging device such as CCD, CMOS or the like to acquire pictorial images in the body cavity while it is moving in the body cavity lumen, converts the image data to a predetermined signal by the signal processor, and transmits the signal by the transmitter towards the receiving antennae 12a to 12h wirelessly.

Further, the receiving antennae 12a to 12h are to detect a signal of image data transmission output wirelessly from the transmitter in the capsule endoscope 2 as a predetermined electrical displacement, and are constituted by a plurality of loop antennae (eight in this example). Each of the antennae 12a to 12h is pasted directly or put into a bag or the like to the predetermined sites for example, right and left flank of abdomen of the subject 3, around epigastric fossa, right and left seventh rib, right and left hypogastric region or the like, using adhesive tape or the like.

Eight cables 5 extending from these receiving antennae 12a to 12h are constituted by cables with good shielding performance, for example, coaxial cables. The length of these cables 5 each is determined in advance for each of corresponding receiving antennae 12a to 12h according to their positions on the body surface. Further, these cables 5 are aligned by a plurality of bundling members 13 so that eight cables may be lined up on the same plane on the way, as shown in FIG. 2, and are pulled into an antenna unit 6b to be electrically connected to a receiving unit 6a of the receiving apparatus 6. Further, cables 5 are designed to be detachable from the antenna unit 6b.

The receiving apparatus 6 includes the receiving unit 6a and the antenna unit 6b, and these are designed to be detachably attached. As shown in FIG. 2, the receiving unit 6a includes a liquid crystal display unit 16; an antenna unit mounting part 17, a viewer cable connector 18, a connector 19 for connection with a cradle 27 which will be described later, or the like. Inside the receiving unit 6a, a circuit member including CF memory for recording image data transmitted via the cable 5 is mounted on a substrate, and a battery pack with a capacity capable of coping with clinical examination continued for lengthy time as long as 8 to 10 hours is loaded in a battery chamber (not shown). In addition to recording of the image data, the receiving unit 6a executes various processings on signals received by the receiving antennae 12a to 12h. The antenna unit mounting part 17 has such a composition that an internal circuit of the receiving unit 6a and the receiving antennae 12a to 12h are electrically connected, while the antenna unit 6b, which has removably attached connector construction, is inserted. Numeral 20 denotes an eject button for removing the antenna 6b.

The viewer cable connector 18 is provided at side face of one side of the receiving unit 6a. The composition is such that if one connector 21a of the viewer cable 21 is attached to the viewer cable connector 18 and the other connector 21b to the viewer 22, images during clinical examination recorded by the receiving unit 6a can be checked by the viewer 22 as needed.

Besides, the workstation 8 primarily has personal computers or the like installed in a hospital, and includes a display device 24, a printer 25, a keyboard 26 or the like, and further includes the cradle 27 for taking image data recorded in CF memory in the receiving unit 6a collectively into a workstation main body 23, and a cradle cable 28 such as USB cable or the like. When the receiving unit 6a is inserted into the cradle 27 and is put into a state where it is electrically connected via the connector 19, the workstation main body 23 takes all image data recorded in CF memory in the receiving unit 6a collectively into the workstation main body 23.

Figure 3:
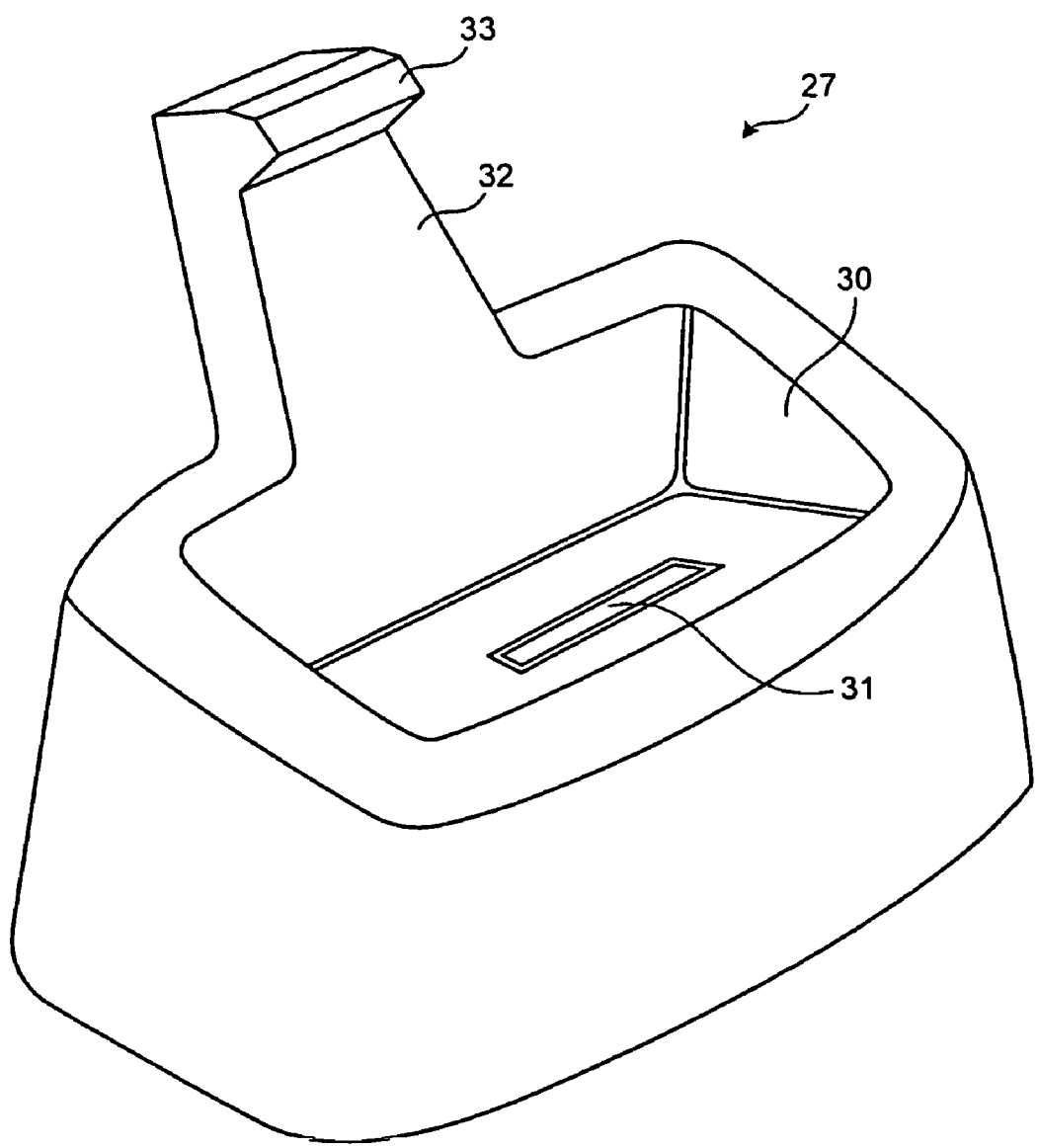
FIG. 3 is a perspective view of the cradle according to the first embodiment.
Figure 4:
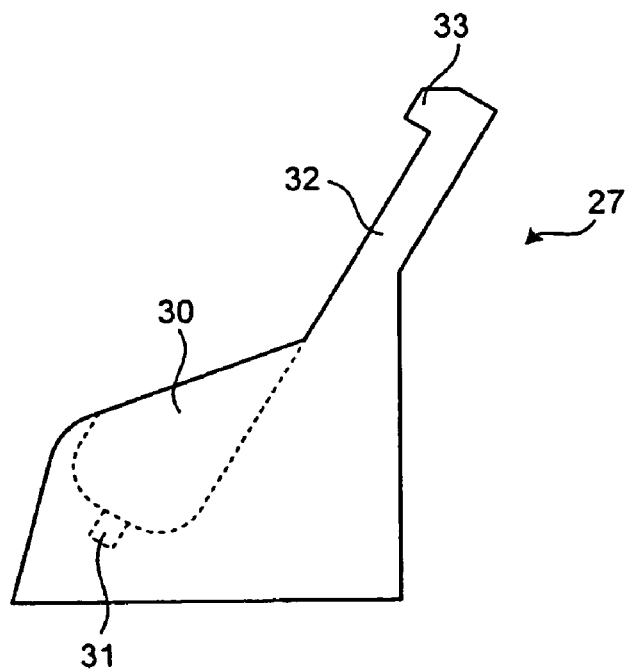
FIG. 4 is a side elevation view of the cradle according to the first embodiment.

Next, the cradle 27 according to the first embodiment will be explained. FIG. 3 is a perspective view of the cradle 27 according to the first embodiment, and FIG. 4 is a side elevation view of the cradle 27 according to the first embodiment. The cradle 27 according to the first embodiment is of stationary type and includes a concave part 30 at center portion thereof for placing the receiving unit 6a of the receiving apparatus 6, a connecting terminal 31 provided at bottom of the concave part 30, a backrest 32 for preventing falling of the receiving unit 6a when the receiving unit 6a is placed, and a protruding portion 33 provided at front edge of the backrest 32.

Figure 5:
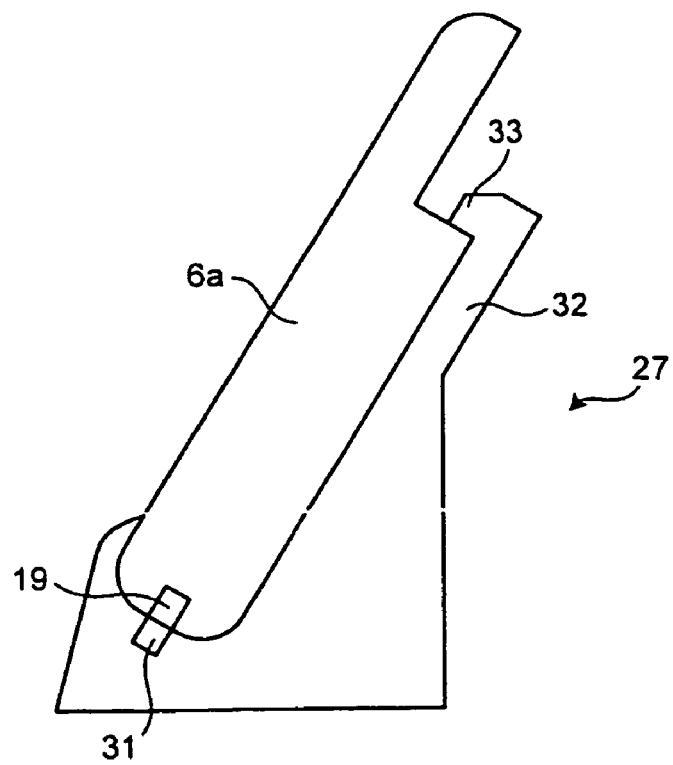
FIG. 5 is a longitudinal sectional view showing a state where a receiving unit is connected to the cradle.

Now, a method for connecting the receiving unit 6a to the cradle 27 will be explained hereafter. FIG. 5 is a longitudinal sectional view showing a state where the receiving unit 6a is connected to the cradle 27. First, the antenna unit 6b is removed from the receiving unit 6a of the receiving apparatus 6 to obtain such a state that receiving antennae 12a to 12h and the receiving unit 6a are electrically separated. Lower end side (connector 19 side) of the receiving unit 6a, which is now in such a state that the antenna unit 6b is removed, is then inserted into the concave part 30. This manipulation allows for engagement of the connector 19 of the receiving unit 6a and the connecting terminal 31 of the cradle 27, and the receiving unit 6a and the cradle 27 are electrically connected.

In a state where the receiving unit 6a is inserted into the concave part 30 of the cradle 27, and the receiving unit 6a and the cradle 27 are electrically connected, the protruding portion 33 is protruding to a portion where the antenna unit 6a is mounted to the receiving unit 6a, as shown in FIG. 5.

Figure 6:
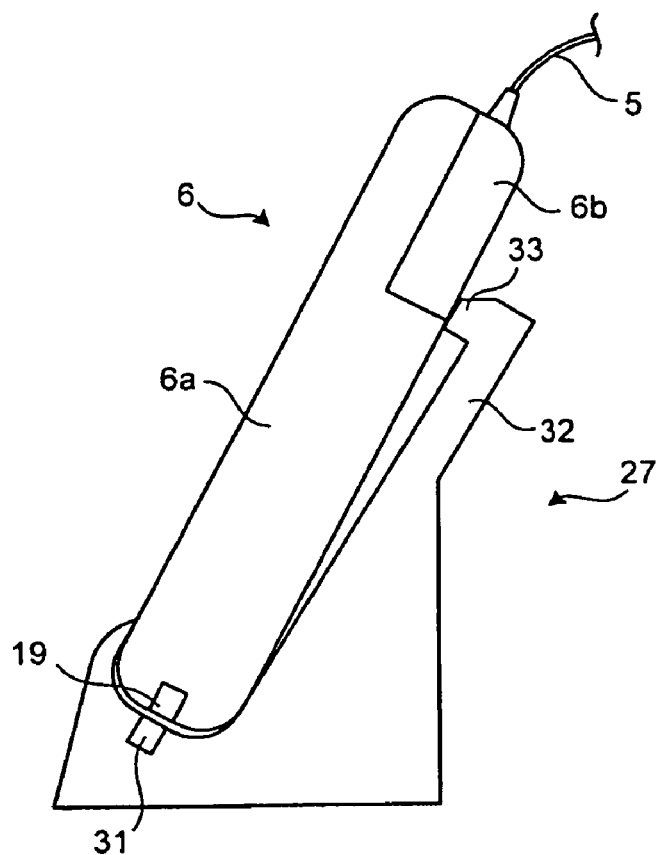
FIG. 6 is a longitudinal sectional view showing a state when the receiving apparatus is about to be connected to the cradle under a state where an antenna unit is mounted to the receiving unit.

Therefore, when it is attempted to connect the receiving apparatus 6 to the cradle 27 while the antenna unit 6b is mounted to the receiving unit 6a, as shown in FIG. 6, the receiving apparatus 6 can not be inserted completely into the concave part 30, and the connector 19 is not engaged with the connecting terminal 31. This means that in a state where the antenna unit 6b is mounted to the receiving unit 6a, the receiving apparatus 6 and the cradle 27 are not electrically connected.

Since the cradle 27 according to the first embodiment has the protruding portion 33 for preventing the receiving apparatus 6 from being electrically connected, in a state where the antenna unit 6b is mounted to the receiving unit 6a, it is possible to prevent the receiving apparatus 6 from being connected to the cradle 27 while the receiving antennae 12a to 12h are connected, thereby maintaining the cradle stably in the connected state.

Second Embodiment

Next, a second embodiment will be explained. Compared with the cradle 27 according to the first embodiment, a cradle 37 according to the second embodiment has no backrest 32, and shapes of the protruding portion 33 and protruding portion 43 are different. Further, constitution of the receiving apparatus 6 or the like are same as those according to the first embodiment, and therefore, like components are identified by the same reference numerals for explanation.

Figure 7:
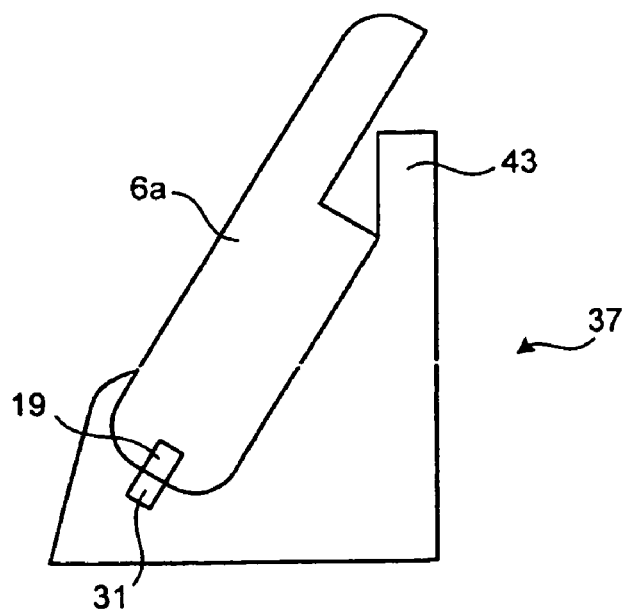
FIG. 7 is a longitudinal sectional view showing a state where the receiving unit according to a second embodiment is connected to the cradle.

FIG. 7 is a longitudinal sectional view showing a state where the receiving unit 6a is connected to the cradle 37. The cradle 37 according to the second embodiment has no backrest 32, and the protruding portion 43 is in a state protruding upwardly from rear side of the cradle 37. As with the first embodiment, when lower end side (connector 19 side) of the receiving unit 6a, from which the antenna unit 6b is removed, is inserted into the concave part 30, the connector 19 of the receiving unit 6a and the connecting terminal 31 of the cradle 37 are engaged, thereby electrically connecting the receiving unit 6a and the cradle 37.

In a state where the receiving unit 6a is inserted into the concave part 30 of the cradle 37, and the receiving unit 6a and the cradle 37 are electrically connected, the protruding portion 43 is, as shown in FIG. 7, protruding to a portion where the antenna unit 6b is mounted to the receiving unit 6a.

Figure 8:
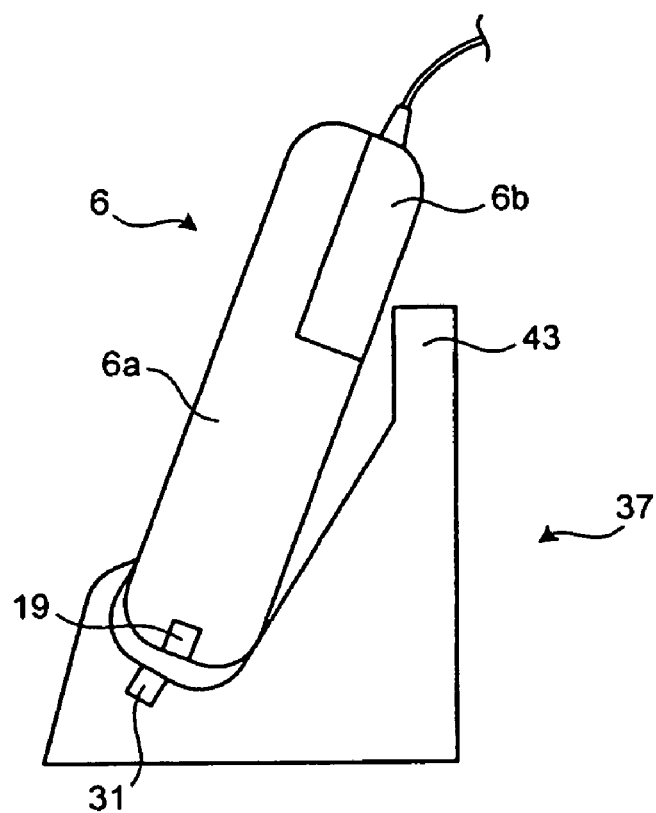
FIG. 8 is a longitudinal sectional view showing a state when the receiving apparatus is about to be connected to the cradle under a state where the antenna unit is mounted to the receiving unit.

Further, when it is attempted to connect the receiving apparatus 6 to the cradle 37 while the antenna unit 6b is mounted to the receiving unit 6a, as shown in FIG. 8, as with the first embodiment, the receiving apparatus 6 can not be inserted completely into the concave part 30, and the connector 19 is not engaged with the connecting terminal 31. This means that in a state where the antenna unit 6b is mounted to the receiving unit 6a, the receiving apparatus 6 and the cradle 37 are not electrically connected.

Since the cradle 37 according to the second embodiment has the protruding portion 43 for preventing the receiving apparatus 6 from being electrically connected, in a state where the antenna unit 6b is mounted to the receiving unit 6a, it is possible to prevent the receiving apparatus 6 from being connected to the cradle 27 while the receiving antennae 12a to 12h are connected, thereby maintaining the cradle stably in the connected state in similar fashion as the first embodiment. Meanwhile, position, shape or the like of protruding portion to be provided to the cradle are not limited to above-mentioned ones as long as the receiving apparatus 6 is prevented from being electrically connected to the cradle in a state where the antenna unit 6b is mounted to the receiving unit 6a.

Third Embodiment

Figure 9:
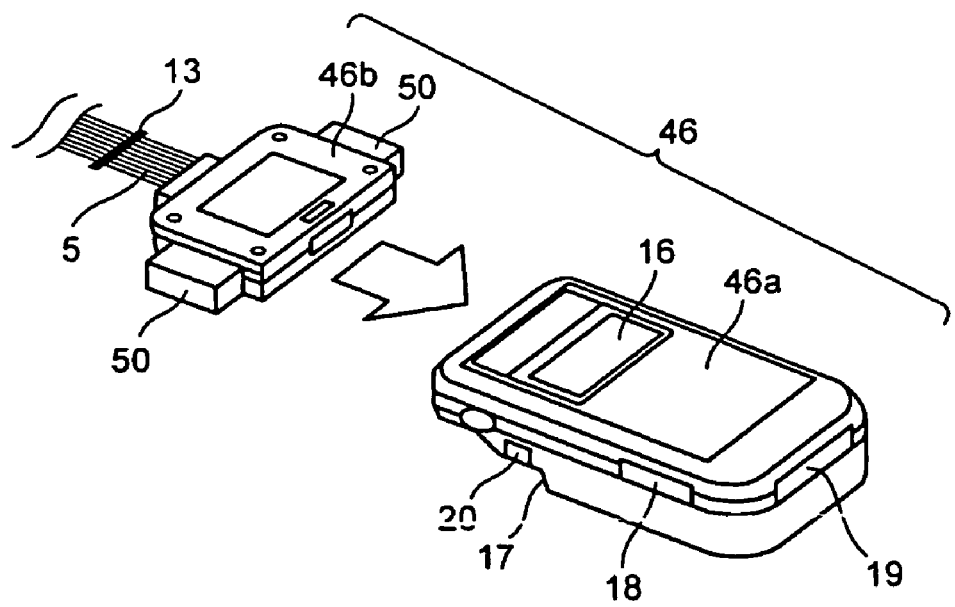
FIG. 9 is a perspective view showing the receiving apparatus according to a third embodiment.

Next, a cradle, receiving apparatus and cradle system including this cradle and receiving apparatus according to a third embodiment will be explained. Meanwhile, components similar to those of the first embodiment are identified by the same reference numerals for explanation. FIG. 9 is a perspective view showing the receiving apparatus 46 according to the third embodiment. Although a receiving unit 46a of the receiving apparatus 46 is similar to the receiving unit 6a according to the first embodiment, an antenna unit 46b has a convex part 50 at both side faces, respectively.

Figure 10:
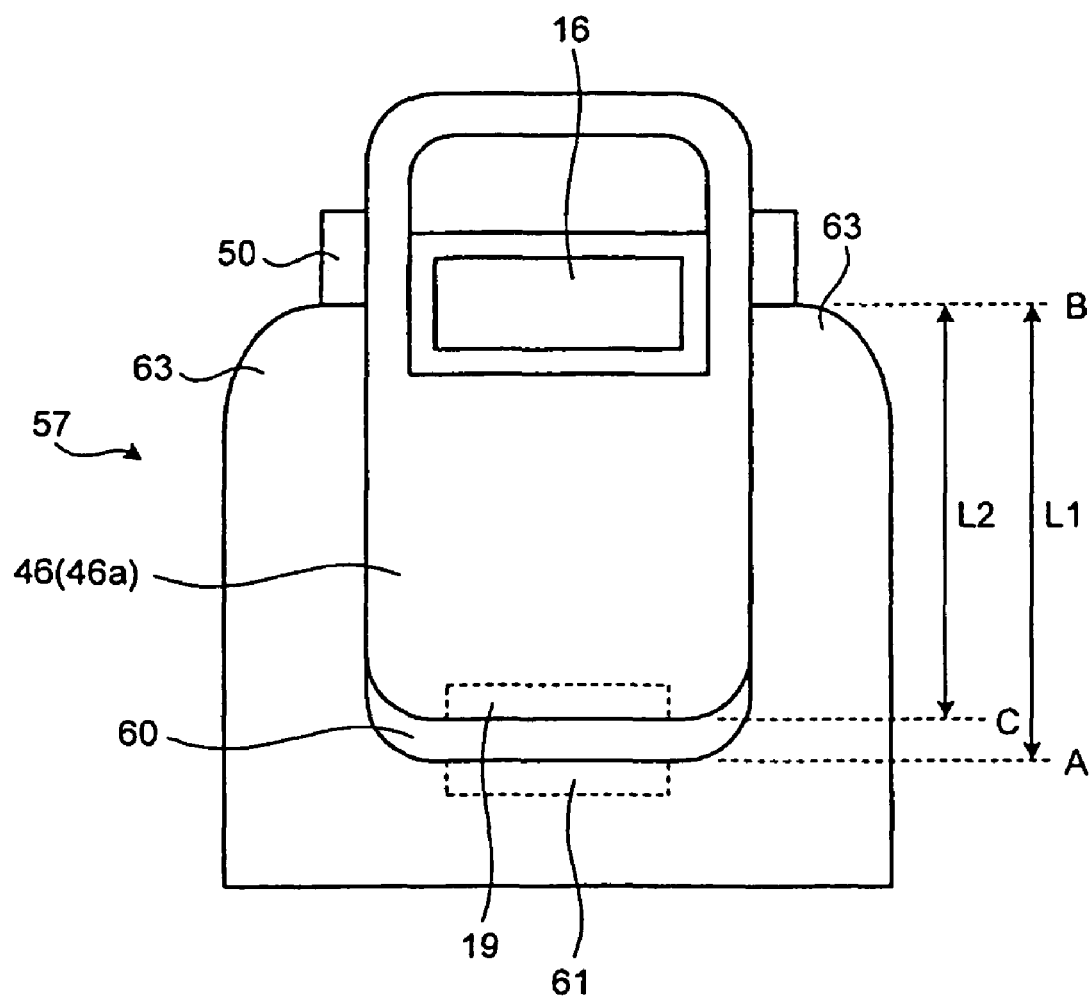
FIG. 10 is a front view showing a state when the receiving apparatus is about to be connected to the cradle according to the third embodiment under a state where the antenna unit is mounted to the receiving unit.

FIG. 10 is a front view showing a state when the receiving apparatus 46 is about to be connected to a cradle 57 according to the third embodiment under a state where the antenna unit 46b is mounted to the receiving unit 46a. The cradle 57 according to the third embodiment has two protruding portions 63 at both ends, and a concave part 60 is formed therebetween. In a state where the antenna unit 46b is removed, the receiving unit 46a is inserted into the concave part 60 to height A to be electrically connected with the cradle 57. On this occasion, the connector 19 of the receiving unit 46a and a connecting terminal 61 of the cradle 57 are engaged. In the meantime, breadth of the receiving unit 46a and antenna unit 46b (excluding convex part 50) according to the third embodiment, and breadth of the concave part 60 are set to be nearly identical.

The receiving unit 46a and antenna unit 46b according to the embodiment are formed such that length L1 from lower end of the receiving unit 46a (height A) to upper end of a protruding portion 63 (height B), in a state where the receiving unit 46a is mounted to the cradle 57, is longer than length L2 from lower end of the receiving unit 46a (height C) to lower end of the convex part 50 (height C), in a state where the antenna unit 46b is mounted to the receiving unit 46a. For this reason, when it is attempted to connect the receiving apparatus 46 to the cradle 57 while the antenna unit 46b is mounted to the receiving unit 46a, upper end of the protruding portion 63 and lower end of the convex part 50 interfere with each other.

Accordingly, when it is attempted to connect the receiving apparatus 46 to the cradle 57 while the antenna unit 46b is mounted to the receiving unit 46a, as shown in FIG. 10, as with the first embodiment, the receiving apparatus 46 can not be inserted completely into the concave part 60, and the connector 19 is not engaged with the connecting terminal 61. This means that in a state where the antenna unit 46b is mounted to the receiving unit 46a, the receiving apparatus 46 and the cradle 57 are not electrically connected.

With the cradle system according to the third embodiment, the antenna unit 46b has the convex part 50, and when it is attempted to connect the receiving apparatus 46 to the cradle 57 while the antenna unit 46b is mounted to the receiving unit 46a, upper end of the protruding portion 63 and lower end of the convex part 50 interfere with each other, and therefore, as with the first embodiment, it is possible to maintain stability of the cradle in connected state. Meanwhile, position, shape or the like of the convex part 50 and protruding portion 63 are not limited to those exemplified in the third embodiment. For example, the convex part 50 may be integrated to rear side of the antenna unit or the protruding portion 63 may be integrated to rear side of the cradle 57.

INDUSTRIAL APPLICABILITY

As mentioned above, the received information transferring apparatus, receiving apparatus and received information transferring system according to the present invention are useful for received information transferring apparatus, receiving apparatus and received information transferring system where connected state is maintained in stable fashion, and is particularly suited for received information transferring apparatus, receiving apparatus and received information transferring system in capsule endoscope system in which information transmitted from capsule endoscope is processed.

The invention claimed is:

1. A received information transferring apparatus, comprising:
    an engagement part for engaging with regard to a unit connection part which allows an antenna unit having at least a receiving antenna to be detachably connected to a receiving unit constituting a receiving apparatus together with the antenna unit; and
    a communication connector that is provided so as to be communicably connected to a connector provided to the receiving unit only when the unit connection part and the engagement part are in an engaged state,
    wherein the engagement part is formed so as to be protruding to a portion where the antenna unit is mounted to the receiving unit, when the receiving unit is mounted to the received information transferring apparatus.

2. The received information transferring apparatus according to claim 1, wherein the engagement part is formed such that a length from a lower end of the receiving unit to an upper end of the engagement part, in a state where the receiving unit is mounted to the received information transferring apparatus, becomes longer than a length from the lower end of the receiving unit to a lower end of a convex part provided to the antenna unit, in a state where the antenna unit is mounted to the receiving unit, and when it is attempted to electrically connect the receiving apparatus, in the state where the antenna unit is mounted to the receiving unit, the upper end of the engagement part and the lower end of the convex part interfere with each other.

3. A method for transferring a received information, the received information being received by a receiving unit with an antenna unit connected thereto, the method comprising:
   attaching the antenna unit to the receiving unit to make the receiving unit unconnectable to a cradle;
   inserting the receiving unit unconnectable to the cradle;
   receiving, in the receiving unit unconnectable to the cradle, information transmitted from a capsule endoscope;
   removing the antenna unit from the receiving unit to make the receiving unit connectable to a cradle;
   inserting the receiving unit connectable to the cradle; and
   electrically connecting the receiving unit to the cradle.

4. The method according to claim 3, wherein the connecting includes engaging a connecting terminal of the receiving unit with a connecting terminal of the cradle.

5. The method according to claim 3, further comprising transferring the received information to an external device via the cradle.

* * * * *